(12) United States Patent
Wong

(10) Patent No.: US 8,313,774 B1
(45) Date of Patent: Nov. 20, 2012

(54) ORAL SOLID COMPOSITION

(75) Inventor: David Wong, Milpitas, CA (US)

(73) Assignee: Magnifica Inc., Fremont, CA (US)

( * ) Notice: Subject to any disclaimer, the term of this patent is extended or adjusted under 35 U.S.C. 154(b) by 0 days.

(21) Appl. No.: 13/533,410

(22) Filed: Jun. 26, 2012

(51) Int. Cl.
  *A61K 9/14* (2006.01)
  *A61K 9/22* (2006.01)
  *A61K 9/26* (2006.01)

(52) U.S. Cl. .................. 424/489; 424/468; 424/469

(58) Field of Classification Search .................. None
See application file for complete search history.

(56) References Cited

U.S. PATENT DOCUMENTS

| | | |
|---|---|---|
| 4,654,296 A | 3/1987 | Held |
| 5,028,433 A | 7/1991 | Ishimaru et al. |
| 5,162,117 A | 11/1992 | Stupak et al. |
| 5,281,420 A | 1/1994 | Kelm et al. |
| 5,514,663 A | 5/1996 | Mandel |
| 5,631,022 A | 5/1997 | Mandel et al. |
| 5,651,983 A | 7/1997 | Kelm et al. |
| 5,656,290 A | 8/1997 | Kelm et al. |
| 5,773,025 A | 6/1998 | Baichwal |
| 5,843,479 A | 12/1998 | Kelm et al. |
| 5,932,245 A | 8/1999 | Wunderlich et al. |
| 5,972,389 A | 10/1999 | Shell et al. |
| 6,174,873 B1 | 1/2001 | Wrenn, Jr. |
| 6,323,193 B1 * | 11/2001 | Somani et al. ................. 514/202 |
| 6,706,283 B1 | 3/2004 | Appel et al. |
| 7,273,624 B2 | 9/2007 | Rosenberg et al. |
| 7,803,748 B2 | 9/2010 | Sung et al. |
| 2003/0185891 A1 | 10/2003 | Crew et al. |
| 2004/0185102 A1 | 9/2004 | Friesen et al. |
| 2004/0197398 A1 | 10/2004 | Friesen et al. |
| 2008/0293801 A1 | 11/2008 | Friesen et al. |
| 2009/0220590 A1 * | 9/2009 | Nkanginieme ............... 424/452 |
| 2010/0068270 A1 | 3/2010 | Turchetta et al. |
| 2012/0087978 A1 | 4/2012 | Nause |

FOREIGN PATENT DOCUMENTS

WO  WO2009/092129  *  7/2009

* cited by examiner

*Primary Examiner* — Daniel Sullivan
*Assistant Examiner* — Rachael E Bredefeld

(57) ABSTRACT

The present invention relates to an oral tablet composition for pharmaceutical use, comprising (1) a particle comprising an amorphous structure and a submicron domain and (2) a pharmaceutically acceptable carrier, wherein the composition is optionally coated.

2 Claims, No Drawings

ORAL SOLID COMPOSITION

TECHNICAL FIELD

The present invention relates to an oral tablet composition for pharmaceutical use comprising (1) a particle comprising an amorphous structure and a submicron domain and (2) a carrier, wherein both amorphous structure and submicron domain comprise a drug, and wherein the particle shows crystalline property.

BACKGROUND OF THE INVENTION

Poor water-solubility is known to be a limiting factor bioavailability. Many attempts have been done with the aim to improving the bioavailability of water-insoluble and water-sparingly soluble drugs. Most such formulations were immediate release in nature as this generally maximizes the amount of drug absorbed. Micronization, solid dispersion and micelle-formation are common techniques used to enhance the drug solubility.

Solid dispersion has been prepared by solvent evaporation, by spray drying, by spraying drug solution onto a carrier, by twin screw extrusion, by melt fusion, by mechanical admixture such as by ball milling and by mechanical admixture at an elevated but non-melting temperature, as described in U.S. Pat. No. 6,706,283.

Solid dispersion has been suggested by several U.S. patents. U.S. Pat. No. 5,281,420 teaches compositions in dosage form comprising a solid dispersion which is a solidified melt mixture consisting of tebufelone, a poloxamer surfactant and other components. The other components are miscible with a melt mixture of components. U.S. Pat. No. 7,273,624 has taught a composition of an active ingredient embedded amorphously in particular. The author emphasizes that there are essentially no crystalline contents of any constituent in their particular embodiment. U.S. Pat. No. 4,654,296 teaches a solid dispersion composition containing dihydropyridien A uniformly dispersed in hydroxypropylmethyl cellulose. U.S. Pat. No. 5,028,433

TECHNICAL FIELD

The present invention relates to an oral tablet composition for pharmaceutical use comprising (1) a particle comprising an amorphous structure and a submicron domain and (2) a carrier, wherein both amorphous structure and submicron domain comprise a drug, and wherein the particle shows crystalline property.

BACKGROUND OF THE INVENTION

Poor water-solubility is known to be a limiting factor bioavailability. Many attempts have been done with the aim to improving the bioavailability of water-insoluble and water-sparingly soluble drugs. Most such formulations were immediate release in nature as this generally maximizes the amount of drug absorbed. Micronization, solid dispersion and micelle-formation are common techniques used to enhance the drug solubility.

Solid dispersion has been prepared by solvent evaporation, by spray drying, by spraying drug solution onto a carrier, by twin screw extrusion, by melt fusion, by mechanical admixture such as by ball milling and by mechanical admixture at an elevated but non-melting temperature, as described in U.S. Pat. No. 6,706,283.

Solid dispersion has been suggested by several U.S. patents. U.S. Pat. No. 5,281,420 teaches compositions in dosage form comprising a solid dispersion which is a solidified melt mixture consisting of tebufelone, a poloxamer surfactant and other components. The other components are miscible with a melt mixture of components. U.S. Pat. No. 7,273,624 has taught a composition of an active ingredient embedded amorphously in particular. The author emphasizes that there are essentially no crystalline contents of any constituent in their particular embodiment. U.S. Pat. No. 4,654,296 teaches a solid dispersion composition containing dihydropyridien A uniformly dispersed in hydroxypropylmethyl cellulose. U.S. Pat. No. 5,028,433 teaches a readily absorbable drug formulation by incorporating to a water-soluble or enteric polymer. U.S. Pat. No. 5,514,663 teaches a composition comprising 3-15 mg of sennosides, wherein the sennosides are in a solid dispersion. U.S. Pat. No. 5,631,022 teaches a composition wherein the drug is in a solid dispersion in a water-soluble carrier. U.S. Pat. No. 5,651,983, U.S. Pat. No. 5,843,479 and U.S. Pat. No. 5,656,290 teach a solid dispersion of bisacodyl on a hydrophilic substrate. U.S. Pat. No. 6,174,873 suggests a solid dispersion comprising a carrier selected from the group consisting of polyethylene glycol, polyvinylpyrrolldone, hydroxypropylmethyl cellulose, phosphatidylcholine, polyoxyethylone hydrogenated castor oil, hydroxypropylmethylcellulose phthalate, carboxymethylethylcellulose, hydroxypropylmethylcellulose, ethyl cellulose and stearic acid.

Application of solid dispersion on oral extended release tablet for treating diseases has been described in U.S. Pat. No. 6,706,283 and other articles. U.S. Pat. No. 5,162,117 teaches a controlled release tablet of flutamide. The core comprises 20-80 percent of flutamide and a carrier capable of forming a solid dispersion with flutamide. U.S. Pat. No. 5,773,025 teaches a bioavailable sustained release oral solid dosage form comprising agglomerated particles of a therapeutically active medicament in amorphous form.

Several articles teach tablet composition comprising nano- or submicron particles. U.S. Pat. No. 5,932,245 suggests a dosage formulation that provides for the release of nanoparticles, wherein the nanoparticles have inner phase and outer phase. Both phases are charged. U.S. Pat. No. 5,972,389 teaches a controlled release oral drug dosage form for releasing a vesicle-containing drug into the stomach, duodenum, and intestinal areas which contain Peyer's patches of a patient, wherein said drug is soluble, but is rendered sparingly soluble when contained in said vesicle, and wherein the vesicle is a member selected from the group consisting of a liposome, nanoparticle, nanosphere and nanocapsule. U.S. Pat. No. 7,803,748 teaches a composition of nanoparticles wherein the nanoparticles enhance paracellular transport of at least one bioactive agent and wherein said nanoparticles are further configured in a tablet form with one or more excipients.

It is known that unstable solid dispersion converts to a crystal form over the time, while nano-particle aggregation or even fusion may happen during the process or storage. Thus, there remains a need for a novel pharmaceutical dosage structure and/or composition comprising an amorphous structure and submicron particle allowing more flexibility for formulation development. A flexible formulation comprising an amorphous structure and submicron particle may allow a reduction of instability during storage or even improved bioavailability compared to conventional tablet dosage forms.

BRIEF SUMMARY OF THE INVENTION

The inventor has found a method to develop a solid composition comprising an amorphous structure and a submicron domain for water insoluble or sparingly soluble drugs, wherein the amount of submicron domain is affected by the amount of non-solvent used in the process.

According, in one aspect the present invention relates to a tablet composition comprising a particle and a pharmaceutically acceptable carrier, wherein the particle comprises an amorphous structure and a submicron domain, and wherein the amorphous structure is a molecular solid dispersion of a drug in a polymeric matrix and the submicron domain is a submicron drug particle. The pharmaceutically acceptable carrier comprises a gelling agent, a binder, a filler and a lubricant, and the tablet composition may exhibit crystalline properties as observed under a polarized microscope. The tablet composition is optionally coated with a film for cosmetic or other purposes. And also, the tablet composition may further comprise a sweetener.

In a further aspect, the invention relates to a method for preparing a particle comprising an amorphous structure and a submicron domain, wherein the particle is prepared by dissolving a drug and a polymer in a co-solvent, adding a non-solvent to precipitate a portion of the drug, drying and milling of the resulting mass.

DETAILED DESCRIPTION OF THE INVENTION

Definitions

As used herein, the term "drug" means a compound intended for use in diagnosis, cure, mitigation, treatment, or prevention of disease in man or other animals. The terms drugs, therapeutics, actives, active ingredient and biological active are inter-changeable. "Optional" or "optionally" means that the subsequently described circumstance may or may not occur, so that the description includes instances where the circumstance occurs and instances where it does not.

Singular forms included in the claims such as "a", "an" and "the" include the plural reference unless expressly stated or the context clearly indicates otherwise.

By "pharmaceutically acceptable" is meant a carrier comprised of a material that is not biologically or otherwise undesirable.

In the present context, the term "hydrophilic" describes that something 'likes water', i.e. a hydrophilic molecule is one that typically is electrically polarized and capable of forming hydrogen bonds with water molecules.

The terms "soluble", "slightly soluble", "sparingly-soluble" and "insoluble" are relative. In general, a substance is said to be soluble if more than 0.1 g of the substance dissolves in 100 mL solvent. In the present context, "slightly soluble", "sparingly-soluble" and "insoluble" are inter-changeable.

In the present context, the term "amphiphilic" in the present context describes a chemical is able to dissolve in an aqueous medium and an organic solvent. For example, polyvinylpyrrolidone is considered as an amphiphilic molecule, as it dissolves in water and in most alcohols.

The terms "solid dispersion" and "amorphous structure" are interchangeable. Solid dispersion, in the present context, denotes the drug molecules dispersed in a polymeric matrix in a solid state.

In this context, solvent is a liquid that dissolves solids resulting in a solution. Non-solvent is a substance incapable of dissolving a given component of a mixture. Thus, water is a non-solvent to water-insoluble drugs such as duloxetine HCl.

The Invention

The present invention provides an oral composition and methods for preparing such compositions. The oral solid compositions are in the form of tablets and may have one or more of the following characteristics: (1) comprising an amorphous structure of a drug substance and a submicron domain of the same drug substance, (2) providing fast or slow release; and (3) optionally coated for appearance, tasking masking, extended-release or delayed-release. According, this invention provides an oral extended-release tablet composition for pharmaceutical use comprising a particle comprising an amorphous structure and a submicron domain and a pharmaceutically acceptable carrier, wherein the amorphous structure comprises drug molecules dispersed in an amphiphilic polymer matrix, wherein the submicron domain is a submicron particle containing essentially a drug, and wherein the a pharmaceutically acceptable carrier comprising a binder, a filler, an extended-release aid, glidant and a lubricant alone or in any combination. The pharmaceutically acceptable carrier may further comprise a drug. The pharmaceutically acceptable carrier may also contain a drug and the composition is optionally film-coated.

Solvent-based method is one of the popular ways to prepare solid dispersion. In such method, a co-solvent is used to intimately dissolve a drug and carrier molecules together to form a solution, and then the solvent is removed by evaporation. The resulting solid is a dispersion of drug molecules in the carrier molecules. In the present invention, a non-solvent (with respect to the drug; miscible to the solvent) is added to the drug-carrier solution. As the solvency to the drug decreases, the solution becomes saturated and a portion of the drug precipitates out. At this stage, the solvent is removed by evaporation to achieve a solid state comprising an amorphous structure and submicron domains. Thus, the particle comprising an amorphous structure and a submicron domain can be obtained by the following steps: dissolving a drug and a polymer in a co-solvent, adding a non-solvent to precipitate a portion of the drug to form a suspension, drying the suspension by a spray-dryer or a rotary evaporator, and then milling of the dried mass to form the particles.

The pharmaceutical composition according to the present invention can be obtained by (1) blending and then (2) compressing the particle comprising the amorphous structure and submicron domains with a pharmaceutically acceptable carrier. In this invention, the pharmaceutical composition is an oral tablet. It can be an extended release tablet or an immediate-release tablet. The composition may further comprise a sweetener and another drug. Under a polarized microscope, the composition shows crystalline properties. The composition may also optionally film-coated for functional or cosmetic purposes. The functional purposes of the film include moisture-barrier, extended-release, delayed-release, taste-masking etc.

In one embodiment, the oral extended-release tablet composition for treating depression comprising: (1) a particle comprising an amorphous structure and a submicron domain, the amorphous structure comprising a water-insoluble drug and an amphiphilic polymer, wherein the submicron domain comprising a water-insoluble drug, (2) a micronized water-insoluble drug, and (3) a pharmaceutically excipient; wherein the drug is duloxetine hydrochloride.

In another embodiment, the oral extended-release tablet composition for treating depression comprising: (1) a particle comprising an amorphous structure and a submicron domain, the amorphous structure comprising a water-insoluble drug and an amphiphilic polymer, wherein the submicron domain comprising a water-insoluble drug, and (2) a pharmaceutically excipient; wherein the particle is prepared by dissolving a drug and an amphiphilic polymer in a co-solvent, adding a non-solvent to precipitate a portion of the drug, drying and then milling of the resulting mass; and wherein the drug is duloxetine hydrochloride. The composition may further comprise a micronized duloxetine hydrochloride particle. The composition may also further comprise a tranquilizer, an antidepressant, a muscle relaxant, guar gum or a mixture thereof.

In a particular embodiment, the oral extended-release tablet composition for treating depression comprising: (1) a particle comprising an amorphous structure and a submicron domain, the amorphous structure comprising duloxetine hydrochloride and an amphiphilic polymer, wherein the submicron domain consisting essentially of duloxetine hydrochloride, (2) a micronized duloxetine hydrochloride particle, and (3) a pharmaceutically excipient; wherein the particle is prepared by dissolving duloxetine hydrochloride and polyvinylpyrrolidone in a co-solvent, adding a non-solvent to precipitate a portion of duloxetine hydrochloride, drying and then milling of the resulting mass. In this particular embodiment, the preferred ratio of the amorphous structure to the submicron domain is 0.1:5 to 1:1, and the composition is optionally film-coated. And, the film is a moisture barrier. The composition may further comprise a sweetener, a tranquilizer, an antidepressant, a muscle relaxant, guar gum or a mixture thereof.

In all embodiments, the composition may further comprise a retarding agent or an extended-release agent. Retarding agent is an agent to sustain the drug release, selected from polymers and copolymers of acrylic and/or methacrylic acid esters, polymers and copolymers of vinylpyrrolidones, polymers and copolymers of vinylacetate, cellulose ethers, cellulose esters, polysaccharides, gums, polyvinyl alcohols, monoglycerides, diglycerides, triglycerides, waxes, proteins or shellac. The preferred retarding agent is hydroxypropylmethylcellulose.

Examples of antidepressants include not limited to aripazole, doxepin, clomipramine, bupropion, amoxapine, nortriptyline, citalopram, trazodone, venlafaxine, selegiline, perphenazine, amitriptyline, escitalopram, chlordiazepoxide, isocarboxazid, phenelzine, desipramine, trazodone, nortriptyline, tranylcypromine, paroxetine, fluoxetine, desvenlafaxine, mirtazapine, desvenlafaxine, mirtazapine, quetiapine, nefazodone, doxepin, trimipramine, olanzapine, imipramine, perphenazine, vilazodone, protriptyline, sertraline and olanzapine.

Examples of tranquilizers include phenothiazines, indoles, thioxanthenes, butyrophenones, piperazine compounds, piperidine compounds and benzodiazepines.

Examples of muscle relaxants include but not limit to carisoprodol, chlorphenesin, chlorzoxazone, cyclobenzaprine, diazepam, metaxalone, and methocarbamol.

The amount of excipient employed will depend upon how much active agent is to be used. One excipient can perform multi-functionally. Examples of excipients include but not limited to retarding agent, binder, filler, diluents, lubricant or a mixture thereof.

Examples of sweeteners include but not limited to glucose, stevia extracts, acesulfame potassium, aspartame, neotame, saccharin and sucralose.

Binders include, but are not limited to, starches such as potato starch, wheat starch, corn starch; microcrystalline cellulose; celluloses such as hydroxypropyl cellulose, hydroxyethyl cellulose, hydroxypropyl methylcellulose, ethyl cellulose, sodium carboxy methylcellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, combinations thereof and other materials known to one of ordinary skill in the art and mixtures thereof.

Fillers or diluents, which include, but are not limited to sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

Lubricants may be selected from, but are not limited to, those conventionally known in the art such as magnesium, aluminum or calcium or zinc stearate, polyethylene glycol, glyceryl behenate, mineral oil, sodium stearyl fumarate, stearic acid, hydrogenated vegetable oil and talc. Glidants include, but are not limited to, silicon dioxide; magnesium trisilicate, powdered cellulose, starch, talc and tribasic calcium phosphate, calcium silicate, magnesium silicate, colloidal silicon dioxide, silicon hydrogel and other materials known to one of ordinary skill in the art.

The pharmaceutical dosage form of the invention can optionally have one or more coatings such as moisture-barrier film coating, sugar coating, enteric coating, bioadhesive coating and other coatings known in the art. These coatings help pharmaceutical formulations to release the drug at the required site of action. In one example, the additional coating prevents the dosage from contacting the mouth or esophagus. In another example, the additional coating remains intact until reaching the small intestine or colon (e.g., an enteric coating).

These coating layers comprises one or more excipients selected from the group comprising coating agents, plasticizers, channeling agents, opacifiers, taste-masking agents, fillers, polishing agents, coloring agents, anti-tacking agents and the like.

Coating agents which are useful in the coating process, include, but are not limited to, polysaccharides such as maltodextrin, alkyl celluloses such as methyl or ethyl cellulose, cellulose acetate, hydroxyalkylcelluloses (e.g. hydroxypropylcellulose or hydroxypropylmethylcelluloses); polyvinylpyrrolidone, acacia, corn, sucrose, gelatin, shellac, cellulose acetate pthalate, lipids, synthetic resins, acrylic polymers, OPADRY® coating systems, polyvinyl alcohol (PVA), copolymers of vinylpyrrolidone and vinyl acetate (e.g. marketed under the brand name of PLASDONE®) and polymers based on methacrylic acid such as those marketed under the brand name of EUDRAGIT®. These may be applied from aqueous or non-aqueous systems or combinations of aqueous and non-aqueous systems as appropriate.

Additives can be included along with the film formers to obtain satisfactory films. These additives can include plasticizers such as dibutyl phthalate, triethyl citrate, polyethylene glycol (PEG) and the like, channeling agents such as surfactants, short-chain water-soluble polymers, salts and the like, antitacking agents such as talc, stearic acid, magnesium stearate and colloidal silicon dioxide and the like, fillers such as talc, precipitated calcium carbonate, polishing agents such as Beeswax, carnauba wax, synthetic chlorinated wax and opacifying agents such as titanium dioxide and the like. All these excipients can be used at levels well known to the persons skilled in the art.

EXAMPLES OF INVENTION

The foregoing examples are illustrative embodiments of the invention and are merely exemplary. A person skilled in the art may make variations and modifications without deviating from the spirit and scope of the invention. All such modifications and variations are intended to be included within the scope of the invention.

Example 1

Duloxetine hydrochloride and polyvinylpyrrolidone are co-dissolved in methanol. Homogenization is applied to the mixture, as purified water is added gradually till the solution turns to turbid. The suspension is then spray-died, and passed through a 20 mesh screen. The screened particle is then mixed with a pharmaceutically acceptable carrier, compressed into a tablet.

Example 2

A portion of metaxalone and polyvinylpyrrolidone are co-dissolved in methanol. Homogenization is applied to the mixture, as purified water is added gradually till the solution turns to turbid. The suspension is then spray-died, and passed through a 20 mesh screen. The screened particle is then mixed with another portion of metaxalone and a pharmaceutically acceptable carrier, compressed into a tablet.

Example 3

A portion of clopidogrel bisulfate and polyvinylpyrrolidone are co-dissolved in methanol. Homogenization is applied to the mixture, as purified water is added gradually till the solution turns to turbid. The suspension is then spray-died, and passed through a 20 mesh screen. The screened particle is then mixed with another portion of metaxalone and a pharmaceutically acceptable carrier, compressed into a tablet.

Example 4

Duloxetine hydrochloride and polyvinylpyrrolidone are co-dissolved in methanol. Homogenization is applied to the mixture, as purified water is added gradually till the solution turns to turbid. The suspension is then spray-died, and passed through a 20 mesh screen. The screened particle is then mixed with bupropion hydrochloride and a pharmaceutically acceptable carrier, compressed into a tablet.

Example 5

Duloxetine hydrochloride and polyvinylpyrrolidone are co-dissolved in methanol. Homogenization is applied to the mixture, as purified water is added gradually till the solution turns to turbid. The suspension is then spray-died, and passed through a 20 mesh screen. The screened particle is then mixed with a tranquilizer and a pharmaceutically acceptable carrier, compressed into a tablet.

I claim:

1. An oral extended-release tablet composition for treating depression comprising: (1) a particle comprising an amorphous structure and a submicron domain, wherein the amorphous structure comprises duloxetine hydrochloride and an amphiphilic polymer, and wherein the submicron domain consists essentially of duloxetine hydrochloride, (2) a micronized duloxetine hydrochloride particle, and (3) a pharmaceutically excipient; wherein the particle comprising an amorphous structure and a submicron domain is prepared by dissolving duloxetine hydrochloride and polyvinylpyrrolidone in a co-solvent, adding a non-solvent to precipitate a portion of duloxetine hydrochloride, drying and then milling of the resulting mass, and wherein the ratio of the amorphous structure to the submicron domain is 0.1:5 to 1:1.

2. The oral extended-release tablet composition for treating depression as claimed in claim 1, wherein the tablet is prepared by direct compression.

* * * * *